United States Patent
Lattner

(10) Patent No.: US 7,332,134 B2
(45) Date of Patent: *Feb. 19, 2008

(54) FLUID BED OXYGENATES TO OLEFINS REACTOR APPARATUS AND PROCESS OF CONTROLLING SAME

(75) Inventor: James R. Lattner, Seabrok, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 92 days.

This patent is subject to a terminal disclaimer.

(21) Appl. No.: 10/814,408

(22) Filed: Mar. 31, 2004

(65) Prior Publication Data

US 2004/0186333 A1 Sep. 23, 2004

Related U.S. Application Data

(62) Division of application No. 10/280,817, filed on Oct. 25, 2002.

(51) Int. Cl.
*B01J 8/26* (2006.01)
*B01J 8/18* (2006.01)

(52) U.S. Cl. ............... 422/145; 422/144; 422/147; 422/110

(58) Field of Classification Search ............... 422/144
See application file for complete search history.

(56) References Cited

U.S. PATENT DOCUMENTS

| 2,892,773 | A | * | 6/1959 | Hirsch et al. ............... 208/213 |
| 3,213,014 | A | * | 10/1965 | Atkinson et al. ............ 208/113 |
| 4,076,796 | A | | 2/1978 | Reh et al. ................... 423/659 |
| 4,092,722 | A | * | 5/1978 | Hofferber et al. ............ 700/273 |
| 4,642,273 | A | | 2/1987 | Sasaki ......................... 429/22 |
| 4,873,390 | A | | 10/1989 | Lewis et al. ................. 585/638 |
| 5,157,181 | A | | 10/1992 | Stine et al. .................. 585/329 |

(Continued)

FOREIGN PATENT DOCUMENTS

WO 01/23500 4/2001

OTHER PUBLICATIONS

Gayubo et al., "Kinetic Modeling of Methanol Transformation into Olefins on a SAPO-34 Catalyst", Ind. Eng. Chem. Res., vol. 39, pp. 292-300 (2000).

(Continued)

*Primary Examiner*—Glenn Caldarola
*Assistant Examiner*—Jennifer A. Leung

(57) ABSTRACT

A reactor apparatus and related method for controlling at least one process variable in a circulating fluid bed oxygenates to olefins reactor system comprising a riser are provided. The process variable is selected from at least one of (i) space velocity, (ii) average reaction temperature, (iii) conversion of reactant, and (iv) average coke level on catalyst. Typically, a corresponding set point for at least one process variable is selected from (1) reactant feed rate, (2) feed enthalpy, (3) reactor temperature-related function, e.g., mid-temperature or rate of temperature rise along a portion of the reactor, and (4) catalyst hold-up in the riser of the reactor. A corresponding manipulated variable is selected from (a) feed flow control valve(s), (b) feed preheat rate, (c) activity of the catalyst in the reactor, and (d) amount of catalyst in the reaction zone. The combination of measured and manipulated variables described here allows for smooth, stable control of the reactor at the optimum performance level.

5 Claims, 5 Drawing Sheets

U.S. PATENT DOCUMENTS

| | | |
|---|---|---|
| 5,952,538 A | 9/1999 | Vaughn et al. |
| 6,023,005 A | 2/2000 | Lattner et al. ............... 585/639 |
| 6,137,022 A | 10/2000 | Kuechler et al. ............ 585/638 |
| 6,166,282 A | 12/2000 | Miller ......................... 585/638 |
| 6,287,522 B1 | 9/2001 | Lomas ........................ 422/144 |
| 6,455,747 B1 | 9/2002 | Lattner et al. |
| 2004/0122273 A1 | 6/2004 | Kabin et al. |

OTHER PUBLICATIONS

Othmer et al., "Fluidization and Fluid-Particle Systems," Reinhold Chemical Engineering Series, New York, pp. 48-59, (1960).

Kunii et al., "Fluidization Engineering," John Wiley & Sons, Inc. New York, pp. 76-80 (1969).

\* cited by examiner

FLUID BED OXYGENATES TO OLEFINS REACTOR APPARATUS AND PROCESS OF CONTROLLING SAME This application is a divisional of U.S. application Ser. No. 10/280,817, filed Oct. 5, 2002.

FIELD OF THE INVENTION

The present invention relates to an oxygenates to olefins reactor apparatus employing a fluid bed reactor and a process for its control.

BACKGROUND OF THE INVENTION

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

Important alternate feeds for the production of light olefins are oxygenates, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The process for converting a feedstock, especially a feedstock containing one or more oxygenates, in the presence of a molecular sieve catalyst composition according to the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In a preferred embodiment of oxygenates to olefins conversion, a fluidized bed process or high velocity fluidized bed process is employed which includes a reactor system, a regeneration system and a recovery system.

In order to optimize operation of oxygenates conversion to light olefins, it is desirable to control various parameters associated with the oxygenate to olefins conversion reactor. Such control can enhance oxygenate conversion and/or selectivity for prime olefins, especially for ethylene and propylene.

U.S. Pat. No. 6,166,282 to Miller teaches a process for converting oxygenates to light olefins in a fast-fluidized bed reactor and further observes that oxygenate conversion processes can be sensitive to reaction variables such as temperature, catalytic activity, and space velocity.

U.S. Pat. No. 5,952,538 to Vaughn et al. discloses an optimal range of space velocities which are suitable for oxygenates to olefin conversion.

Gayubo, et al, *Ind. Eng. Chem. Res.* 2000, 39, 292-300, disclose that in conversion to olefins, higher average reaction temperatures at a given coke level on the catalyst increases selectivity to ethylene.

U.S. Pat. No. 6,137,022 to Kuechler et al. discloses oxygenates to olefins conversion in the presence of silicoaluminophosphate molecular sieve-containing catalyst which maintains an optimal feedstock conversion between 80% and 99% under conditions effective to convert 100% of the feedstock when the reaction zone contains at least 33 volume percent of the silicoaluminophosphate molecular sieve.

U.S. Pat. No. 6,023,005 discloses the importance of maintaining optimal average coke levels on oxygenates to olefins conversion catalyst to effect improved lower olefin selectivity.

Control of the above-noted variables is shown as useful for optimizing performance of an oxygenates to olefins reactor. However, there are several problems encountered when attempting to select a control scheme for controlling space velocity, average reaction temperature, conversion of reactant and average coke level on catalyst. For example, measurement of the coke level on catalyst is difficult inasmuch as a sample of catalyst must be withdrawn and analyzed by a laboratory method. There does not currently exist a reliable means to continuously monitor the coke level on catalyst inside of a reactor. A similar problem exists with the measurement of the reactant conversion level. Control engineers generally prefer to use more reliable measured variables, e.g., temperature, for direct control of a process rather than conversion measurement devices.

Thus, a simple and effective control method is needed for controlling oxygenates to olefins reactor systems that does not rely directly on the measurement of variables that are difficult to obtain or which are inherently unreliable in their measurement. Furthermore, it would be desirable to provide a method for controlling oxygenate to olefins reactor systems which utilizes select manipulated and controlled variables so that the response in a measured variable of the control system occurs shortly after a change to the manipulated variable.

SUMMARY OF THE INVENTION

In one aspect, the present invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring a set variable selected from at least one of (1) reactant feed rate, (2) feed enthalpy, (3) a reactor temperature-related function, e.g., reactor mid-temperature or rate of temperature rise along a portion of the reactor, and (4) catalyst hold-up in the riser of the reactor, said set variable functionally corresponding to a process variable selected from at least one of i) space velocity, ii) average reaction temperature, iii) conversion of reactant, and iv) average coke level on catalyst; comparing said measured set variable with an optimal set variable to provide a signal which is a function of the difference between said measured set variable and said optimal set variable; adjusting as a function of said signal a corresponding manipulated variable selected from at least one of a) at least one feed flow control valve, b) feed preheat rate, c) activity of the catalyst in the reactor, and d) amount of catalyst in the reaction zone, to improve at least one of light olefin production rate and light olefin selectivity, e.g., ethylene and/or propylene selectivity.

For present purposes, light olefin production rate is defined as the mass rate of ethylene and propylene produced from a particular reactor system. In an embodiment of the present invention, a reactor temperature-related function is defined as a function of one or more temperature measurements taken along the length of a reactor.

Another aspect of the invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring a reactant feed rate as a set variable functionally corresponding to i) space velocity as a process variable; comparing said measured set variable with an optimal set variable to provide a signal which is a function of the difference between said measured set variable and said optimal set variable; adjusting as a function of said signal a) at least one feed flow control valve as a corresponding manipulated variable, to improve at least one of light olefin production rate and light olefin selectivity.

In another aspect, the present invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring feed enthalpy as a set variable functionally corresponding to average reaction temperature as a process variable; comparing said measured set variable with an optimal set variable to provide a signal which is a function of the difference between said measured set variable and said optimal set variable; adjusting as a function of said signal feed preheat rate as a corresponding manipulated variable, to improve at least one of light olefin production rate and light olefin selectivity.

In still another aspect, the present invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring a reactor temperature-related function, e.g., reactor mid-temperature or rate of temperature rise along a portion of the reactor, as a set variable functionally corresponding to conversion of reactant as a process variable; comparing said measured set variable with an optimal set variable to provide a signal which is a function of the difference between said measured set variable and said optimal set variable; adjusting as a function of said signal activity of the catalyst in the reactor as a corresponding manipulated variable, to improve at least one of light olefin production rate and light olefin selectivity.

In another aspect, the present invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring a reactor temperature-related function, e.g., reactor mid-temperature or rate of temperature rise along a portion of the reactor, as a set variable functionally corresponding to conversion of reactant as a process variable; comparing said measured set variable with an optimal set variable to provide a signal which is a function of the difference between said measured set variable and said optimal set variable; and adjusting, as a function of said signal, the catalyst holdup in the riser to improve at least one of light olefin production rate and light olefin selectivity.

In still yet another embodiment, the present invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring reactor temperature at a plurality of locations along the reactor as a set variable functionally corresponding to conversion of reactant as a process variable; comparing said measured set variable with an optimal set variable to provide a signal which is a function of the difference between said measured set variable and said optimal set variable; and adjusting, as a function of said signal, activity of the catalyst in the reactor as a corresponding manipulated variable, to improve at least one of light olefin production rate and light olefin selectivity.

In still another embodiment, the present invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring a reactor temperature-related function, e.g., reactor mid-temperature or rate of temperature rise along a portion of the reactor, as a set variable functionally corresponding to conversion of reactant as a process variable; comparing said measured set variable with an optimal set variable to provide a signal which is a function of the difference between said measured set variable and said optimal set variable; and adjusting, as a function of said signal, the catalyst holdup in the riser to improve at least one of light olefin production rate and light olefin selectivity.

In yet another aspect, the present invention relates to a process for controlling a fluid bed oxygenates to olefins reactor which comprises: contacting an oxygenate-containing feedstock in a reaction zone in the presence of a molecular sieve oxygenates to olefins conversion catalyst under oxygenate conversion conditions; measuring catalyst hold-up in the riser of the reactor as a set variable functionally corresponding to average coke level on catalyst as a process variable, comparing said measured set variable with an optimal set variable to provide a signal which is a function of the difference between said measured set variable and said optimal set variable; adjusting as a function of said signal, amount of catalyst in the reaction zone as a corresponding manipulated variable, to improve at least one of light olefin production rate and light olefin selectivity.

In yet still another aspect, the present invention relates to a process for controlling a fluid bed oxygenates to olefins reactor which comprises:

contacting an oxygenate-containing feedstock in a reaction zone in the presence of a molecular sieve oxygenates to olefins conversion catalyst under oxygenate conversion conditions; measuring (1) reactant feed rate, (2) feed enthalpy, (3) a reactor temperature-related function, e.g., reactor mid-temperature or rate of temperature rise along a portion of the reactor, and (4) catalyst hold-up in the riser of the reactor, as set variables functionally corresponding to process variables i) space velocity, ii) average reaction temperature, iii) conversion of reactant, and iv) average coke level on catalyst; comparing said measured set variables with corresponding optimal set variables to provide signals each of which is a function of the difference between each respective measured set variable and each corresponding optimal set variable; adjusting as a function of said signals a) at least one feed flow control valve, b) feed preheat rate, c) activity of the catalyst in the reactor and d) amount of catalyst in the reaction zone, as corresponding manipulated variables, to improve at least one of oxygenate conversion and light olefin selectivity.

In another aspect, the present invention relates to a process for controlling an oxygenates to olefins fluidized bed reactor which comprises: contacting an oxygenate-containing feedstock in a reaction zone in the presence of a molecular sieve oxygenates to olefins conversion catalyst under oxygenate conversion conditions; determining an optimized value of a primary variable measurable property; selecting a secondary variable measurable property which is more readily measurable or more reliably measurable than said primary variable measurable property and determining a set point for said secondary variable measurable property corresponding to said optimized value of the primary variable measurable property; measuring said secondary variable measurable property; comparing said measured secondary variable measurable property with said set point for said secondary variable measurable property corresponding to said optimized value of the primary variable measurable property to provide a signal which is a function of the difference between said measured secondary variable measurable property and said set point corresponding to said optimized value of the primary variable measurable property; and adjusting as a function of said signal a corresponding manipulated variable.

In a preferred embodiment of this aspect of the invention, the primary variable measurable property is selected from the group consisting of 1) desired production rate, 2) temperature-related product selectivities, 3) conversion of reactant, and 4) space velocity, said secondary variable measurable property is selected from i) total feed rate, ii) feed enthalpy, iii) reactor temperature-related function and iv) catalyst holdup, and said manipulated variable is selected from at least one of a) at least one feed flow control valve, b) feed preheat rate, c) activity of the catalyst in the reactor (regeneration rate), and d) catalyst circulation slide control valve, and further wherein 1), i) and a); 2), ii) and b); 3), iii) and c); and 4), iv) and d) represent corresponding sets of variables.

In yet another aspect, the present invention relates to an oxygenates to olefins fluidized bed reactor apparatus for converting an oxygenate feed to olefins in a riser reactor which comprises: an oxygenate feed line communicating with a riser reactor feed inlet to said riser reactor; a preheater through which said oxygenate feed line passes for at least partially vaporizing said feed by heat exchange with a fluid heating medium flowing through said preheater; said riser reactor further comprising a riser reactor outlet for riser reactor effluent containing solid catalyst particles and olefins-containing vapor; a disengaging vessel for receiving said riser reactor effluent and separating at least some of said solid catalyst particles from said effluent, said disengaging vessel further comprising a disengaging vessel outlet at an upper portion of said vessel for removing said olefins-containing vapor; a catalyst circulation line running downward from a lower portion of said disengaging vessel to a lower portion of said riser reactor; a regenerator comprising a lower inlet for introducing a regeneration medium, an upper outlet for regenerator flue gas, said regenerator further comprising a catalyst transport line running downwardly from a lower portion of said disengaging vessel to a regenerator catalyst inlet, and a catalyst transport line extending downwardly from a regenerated catalyst outlet and intersecting with a lift gas riser; said lift gas riser having an upper outlet communicating with said disengaging vessel and a lower lift gas inlet; and said reactor apparatus further comprising at least one of:

A) a heating medium flow control valve controlling the flow of said fluid heating medium through said preheater, which heating medium flow control valve is manipulated as a function of temperature of said feed measured at a point between said preheater and said riser reactor feed inlet;

B) an oxygenate feed flow control valve controlling the flow of said feed from said preheater to said reactor inlet which is manipulated as a function of feed flow measured at a point between said preheater and said riser reactor inlet;

C) a catalyst circulation control valve controlling circulation of catalyst from said disengaging vessel to said riser reactor, said catalyst circulation valve being manipulated as a function of the difference in pressure between an upper portion of said riser reactor and a lower portion of said riser reactor; and D) a regenerator catalyst circulation control valve controlling the passage of catalyst from said regenerated catalyst outlet to said lift gas riser, said regenerator catalyst circulation control valve being manipulated as a function of riser reactor temperature.

DETAILED DESCRIPTION OF THE INVENTION

Oxygenate to Olefins Reactor Apparatus

Figure 1:
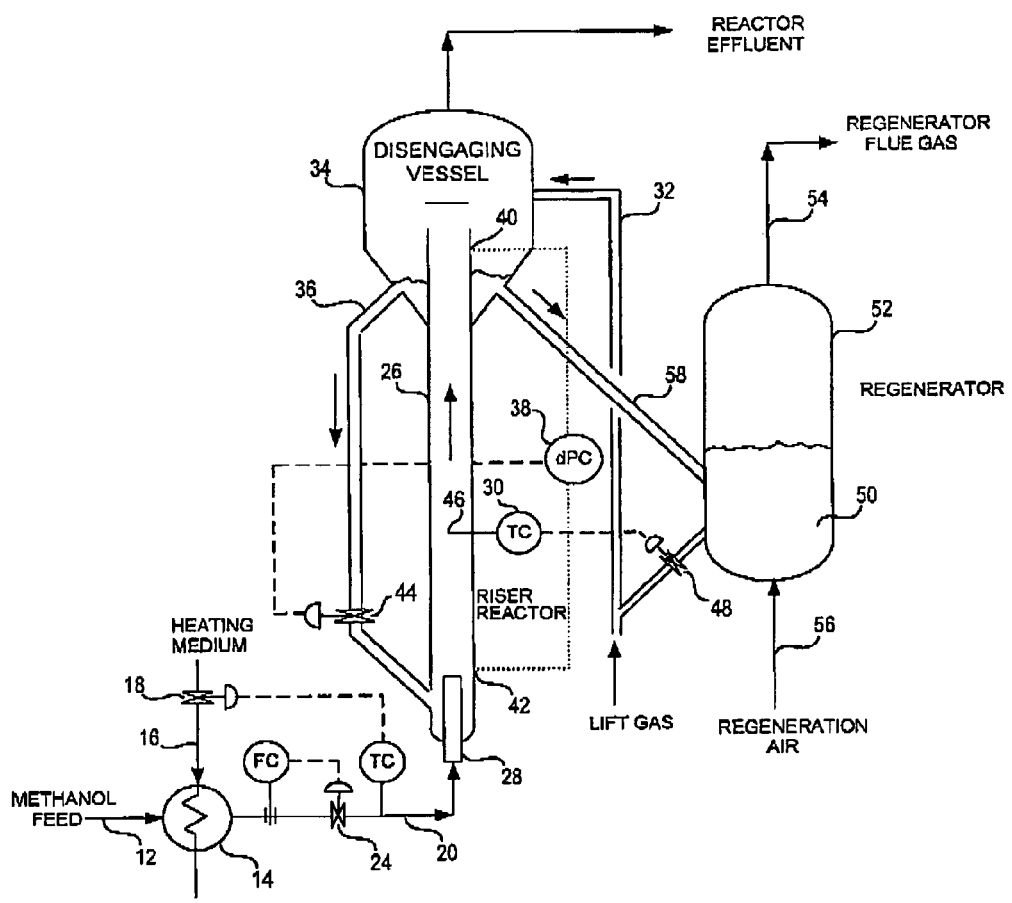
FIG. 1 depicts an oxygenates to olefins circulating fluid bed reactor control scheme in accordance with the present invention.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960,.and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s). Preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

Oxygenate to Olefins Process

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, incorporated herein by reference, addition of aromatics) or mixtures thereof, preferably propylene, butylene, pentylene, and other hydrocarbons having 4 or more carbon atoms, or mixtures thereof.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is selected from group 13 (IIIA), groups 8, 9 and 10 (VIII) elements) from the Periodic Table of Elements), and a molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are disclosed in U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system, where an excess of oxygen is maintained in the regenerator. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336-337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator where an excess flow of catalyst is maintained such that the coke is only partially removed per pass through the regenerator. This is referred to as the partial regeneration mode.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 weight percent coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels of individual catalyst particles.

The present invention solves the current needs in the art by providing a method for converting a feed including an oxygenate to a product including a light olefin. The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

A preferred embodiment of a reactor system for the present invention is a circulating fluid bed reactor with continuous regeneration, similar to a modern fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently or continuously, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a desired coke content on catalyst in the reactor.

Reactor Control

As noted earlier, the operation of an oxygenates to olefins-reactor can be optimized by controlling several important variables associated with the reactor.

Control of the reactor can be effected by measuring a variable, comparing the variable with its corresponding optimal value, selected depending on the outcome desired, deriving a signal based on the comparison, and utilizing the signal to manipulate a manipulated variable. An analogy to this control scheme can be found in speed control devices commonly found in automobiles, wherein the speed represents the measured variable, the speed setting represents the corresponding optimal value and the throttle position represents the manipulated variable. Measured speed is compared with the speed setting to provide a signal that is then used to manipulate the throttle setting to provide a measured value (speed) approximating the optimal value.

Optimal value for present purposes can be set by factoring in desired outcomes of the reactor operator, especially in terms of product characteristics, such as lower olefins content, e.g., ethylene selectivity or propylene selectivity, and/or oxygenate conversion. Other desired outcomes by the operator, or reactor operating limitations, e.g., temperature, pressure, and space velocity may be used to set optimal values or ranges of values for a measured variable. Additional guidance in setting such values can be found in U.S. Pat. No. 4,076,796, U.S. Pat. No. 6,287,522 (dual riser), *Fluidization Engineering*, D. Kunii and O. Levenspiel, Robert E. Krieger Publishing Company, New York, N.Y. 1977, *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), U.S. patent application Ser. No. 09/564,613 filed May 4, 2000 (multiple riser reactor), which are all herein fully incorporated by reference.

The present invention provides a simple and effective method for controlling oxygenates to olefins reactor systems that does not rely directly on the measurement of variables that are difficult to obtain, or which are inherently unreliable in their measurement. Furthermore, the present invention provides a method for controlling oxygenate to olefins reactor systems which utilizes select manipulated and controlled variables so that the response in a measured variable of the control system occurs shortly after a change to the manipulated variable.

In general, the following variables should be controlled in an, oxygenate to olefins reactor system: space velocity (defined as the weight feed rate of reactant divided by the weight of active catalyst ingredient in the reactor), average reaction temperature (which, coupled with the average coke level on the catalyst, infra, determines the product selectivity), conversion of reactant (prime olefin product selectivity is generally favored by low conversions, however the cost of recovering and recycling unreacted feed generally favors high conversion—thus an optimal conversion level exists for a given set of production needs and economic conditions), and average coke level on catalyst (prime olefin product selectivity is favored by high coke levels, but activity is reduced as coke is increased).

U.S. Pat. No. 5,952,538 to Vaughn et al., incorporated herein by reference in its entirety, discloses optimal ranges of parameters, including space velocities, which are suitable for oxygenates to olefin conversion in the present invention. According to an embodiment of the present invention, the olefins are produced at temperatures of about 400° C. or higher. Preferred reactors are co-current riser reactors and short contact time countercurrent free-fall reactors in which an oxygenate feedstock can be contacted with a molecular sieve catalyst at a weight hourly space velocity (WHSV) of at least about 20 hr$^{-1}$, preferably in the range of from about 20 hr$^{-1}$ to 1000 hr$^{-1}$, and most preferably in the range of from about 20 hr$^{-1}$ to 500 hr$^{-1}$. Because the catalyst or the feedstock may contain other materials which act as inerts or diluents, the WHSV is calculated on the weight basis of the oxygenate feed and the molecular sieve used.

Gayubo, et al, *Ind. Eng. Chem. Res.* 2000, 39, 292-300, disclose that in conversion to olefins, higher average reaction temperatures at a given coke level on the catalyst increases selectivity to ethylene. For the present invention average reaction temperatures for optimal selectivity of oxygenate to ethylene can range from 300° to 550° C.

U.S. Pat. No. 6,137,022 to Kuechler et al., incorporated herein by reference in its entirety, discloses oxygenates to olefins conversion in the presence of silicoaluminophosphate molecular sieve-containing catalyst which maintains an optimal feedstock conversion between 80% and 99% under conditions effective to convert 100% of the feedstock when the reaction zone contains at least 33 volume percent of the silicoaluminophosphate molecular sieve.

U.S. Pat. No. 6,023,005 to Lattner et al., incorporated herein by reference in its entirety, discloses the importance of maintaining optimal average coke levels on oxygenates to olefins conversion catalyst to effect improved lower olefin selectivity. Such levels, suited to use in the present invention comprise an amount of at least about 2 wt % carbonaceous deposits, preferably in the range of from about 2 wt % to about 30 wt % carbonaceous deposits, based on the weight of the total reaction volume of coked catalyst. Desirable carbonaceous deposits—even if they comprise over 30 wt % of the total reaction volume of molecular sieve catalyst—are carbonaceous deposits which primarily block portions of the surface of the catalyst that are not selective to the production of $C_2$-$C_3$ olefins.

There are many potential candidates for controlled variables in an oxygenates to olefins reactor system. These include space velocity, coke level on catalyst, catalyst holdup, catalyst recirculation rate, proportion of vapor and liquid feed rates, total feed rate, feed temperature, catalyst regeneration rate, average reaction temperature, and other reactor temperature related functions, e.g., a function of one or more temperature measurements along the longitudinal axis of the reactor. In one embodiment of the invention such functions can be directly related to the reactor temperatures themselves, e.g., reactor inlet temperature, reactor effluent temperature, or at least one intermediate reactor temperature themselves. Alternatively, these functions can be related to differences between such reactor temperatures, e.g., a differential of reactor temperature along a portion of the reactor length.

Despite the plethora of potential controlled variables, there are only four variables that can be independently controlled. The remaining variables are determined by these four controlled variables. Thus there are just four "degrees of freedom" in the control of the reactor. Should the following four variables be selected as controlled variables—total feed rate, average reactor temperature, coke on catalyst, and conversion—any other variable, such as the catalyst regeneration rate, cannot also be specified. Rather, the catalyst regeneration rate will be fixed by the selection of the original four variables.

Based on a careful review of the interactions between the possible controlled and manipulated variables, the present invention provides a control method that achieves direct, fast response for smooth, stable control of the oxygenates to olefins (OTO) reactor at its maximum performance level, which is set out in TABLE 1 below.

TABLE 1

Method of Controlling an MTO Reactor

| Primary Variable— Measurable Property (Infrequent or less reliable variable measurement) | Secondary Variable Measurable Property (Used to adjust the set point for the controlled variable) | Which manipulates the process parameter: |
|---|---|---|
| (1) Desired Production Rate | Total Feed Rate | Feed flow control valve(s) |
| (2) Temperature-related product selectivities | Feed Enthalpy | Rate of total heat input to feed |
| (3) Conversion of reactant | (a) Reactor temperature (at some optimum axial position) (b) Reactor temperature related function | Catalyst activity (regeneration rate) (also corresponds to average coke level on catalyst in the reactor) |
| (4) Space velocity | Catalyst holdup | Catalyst circulation slide control valve |

Note that in order for (3)(a) to work properly, there must be very stable control of (2) and the reactor must approach plug flow behavior. Method (3)(b) is less susceptible to variations in (2). With this method, a temperature profile is measured over a portion of the reactor.

The present invention thus relates to a method for controlling an oxygenates to olefins fluidized bed reactor which comprises:

determining an optimized value of a primary variable measurable property, selecting a secondary variable measurable property which is more readily measurable or more reliably measurable than said primary variable measurable property and determining a set point for said secondary variable measurable property corresponding to said optimized value of the primary variable measurable property;

measuring said secondary variable measurable property;

comparing said measured secondary variable measurable property with said set point for said secondary variable measurable property corresponding to said optimized value of the primary variable measurable property to provide a signal which is a function of the difference between said measured secondary variable measurable property and said set point corresponding to said optimized value of the primary variable measurable property; and adjusting as a function of said signal a corresponding manipulated variable.

For present purposes, the term "feed enthalpy" refers to the heat content of the combined total feed streams containing reactants to the reactor. The total feed of reactants may consist of a combination of both vapor and liquid streams. For example, the specific enthalpy (e.g., Joules/g-mole) of a saturated vapor stream at a given temperature will be higher than the combined specific enthalpy of a mixture of a saturated vapor and liquid feed at the same temperature.

For present purposes, the term "conversion" is defined on the basis of disappearance of reactant. In the specific case of methanol to olefins (MTO), the reactant is generally defined as the total of methanol plus dimethyl ether (DME). Thus, for the purposes of calculating conversion, both the methanol and DME are measured in the reactor effluent and combined to determine the disappearance of reactant.

For present purposes, "catalyst activity" is determined by the level of coke on the catalyst. When catalyst activity is the manipulated variable, then catalyst activity is manipulated by adjusting the rate at which coke is removed from the overall process. The method of adjusting the rate of coke removal will depend on the mode of regeneration. There are two basic modes of regeneration (further discussed in U.S. Pat. No. 6,023,005), referred to as full and partial regeneration modes. These are further defined below, along with the method of adjusting catalyst activity in each mode.

For present purposes, "full regeneration mode" relates to a mode of regeneration where excess oxygen is maintained in the regenerator, and coke is the limiting reactant. The coke level on catalyst leaving the regenerator will be low in this mode, less than about 2%. In this mode of regeneration, the catalyst activity in the reactor is adjusted by adjusting the flow of the limiting reactant, which is coke on the catalyst. This adjustment can be carried out by manipulating the catalyst flow rate to/from the reactor and regenerator. Increasing the catalyst flow rate to/from the regenerator will increase the activity of catalyst in the reactor, while decreasing the catalyst flow rate to/from the regenerator will decrease the activity of catalyst in the reactor.

For present purposes, "space velocity" is defined here on a weight hourly basis, and has units of $hr^{-1}$:

$$\frac{\text{Mass flow rate of reactant feed per hour}}{\text{Mass of active catalyst ingredient in the reactor}}$$

For present purposes, "catalyst holdup" is the amount of catalyst in the fluid bed reaction zone at any time. It is determined by measuring the differential pressure over the height of the reaction zone. This determination assumes the weight of gas and the frictional resistances are negligible compared to the weight of solids. The mass of solids is then calculated by:

$$\frac{\text{(Differential pressure over height of reaction zone)} \times \text{(Cross-sectional area)}}{\text{Acceleration of gravity}}$$

One skilled in the art will recognize that if the reactor is designed with varying cross-sectional areas, then several pressure measurements must be made and an integration of the differential pressure and cross sectional areas should be made to determine the total mass of solids in the reactor. Once the holdup of solids is calculated, the weight of active ingredient can be determined from knowledge of the weight fraction of active ingredient and the weight fraction of coke on the catalyst as follows:

(total mass solids)×(1-wt fraction coke on solids)× (wt fraction active ingredient in catalyst).

The weight fraction of active ingredient in the catalyst generally does not change appreciably over time, and the weight fraction of coke is a small fraction that changes little with time. Therefore, from a process control standpoint, the corrections for active ingredient and coke content are not important, and the simple reactor differential pressure can be used as an indication of the catalyst mass within the reaction zone.

For present purposes, "rate constant" represents the value of the constant, k, in the assumed expression for the reaction rate, here assumed to be a first order rate expression: $r_A=kC_A$. Integration of this equation, assuming plug flow behavior of the gas flow through the reactor and ignoring volume expansion, gives the following expression for calculation of the rate constant:

$$k = \frac{\ln(1 - X_A)}{\tau},$$

where $r_A$ is the specific reaction rate based on catalyst volume [kg-mole/sec-m$^3$], $C_A$ is the reactant concentration (kg-moles reactant/volume gas), $X_A$ is the conversion of reactant, and $\tau$ is the space time [sec], defined as the volume of active catalyst ingredient divided by the volumetric feed rate of reactant (at average reaction temperature and pressure), and k is the reaction rate constant [sec$^{-1}$].

For present purposes, "residence time" of a catalyst particle in the reactor is the time between a regenerated catalyst particle entering the reactor, and the time that it leaves the reactor to return to the regenerator. Since the flow of catalyst particles through the reactor is well-mixed, there will be a distribution of residence times for the various catalyst particles in the reactor.

Figure 2:
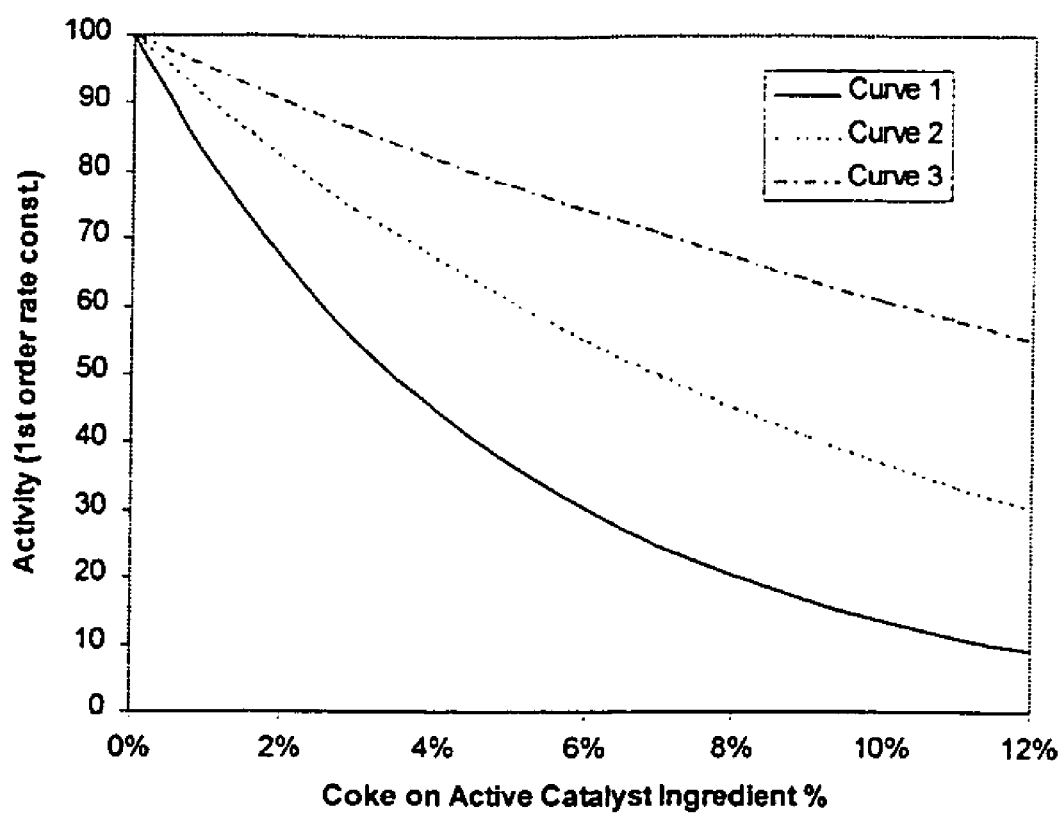
FIG. 2 depicts catalyst activity as a function of the amount of coke on the catalyst for steady stage operation, high level coked catalyst which has been partially regenerated, and fully regenerated catalyst that has been allowed to coke uniformly.

The present invention is of particular utility inasmuch as it can be used to overcome difficulties associated with controlling catalyst activity based on a measurement of the coke level on the catalyst in the reactor. FIG. 2 is a graph depicting the qualitative relationship between the measured coke level and the activity of the catalyst at the different operating modes.

At steady state operation of a reactor, the catalyst in the reactor will consist of a mixture of catalyst particles having various coke levels, due to the residence time distribution of the catalyst particles. When a measurement is taken, many particles are analyzed simultaneously so that the measurement represents the average coke level on the catalyst. The relationship between this measurement and the overall catalyst activity is shown in Curve 1 (the bottom curve) of FIG. 2.

In the full regeneration mode, each catalyst particle enters the reactor with a very low coke level, and thus a high activity. As an individual particle cokes up, it follows an activity relationship expressed by Curve 3 (the upper curve) of FIG. 2. The activity of an individual particle following Curve 3 is higher for a given coke level than the average activity of the reactor at steady state at the same average coke level. Freshly regenerated catalyst is many times more active than the activity of the steady state catalyst composition. This result is due to the exponential decay relationship for coke level versus activity. For the steady state catalyst composition, there is a large fraction of catalyst particles with a high coke level. These particles contribute to the average coke content in the reactor, but do not contribute significantly to the overall activity.

A similar behavior is exhibited in the partial regeneration mode. Partially regenerated catalyst is more active than steady state catalyst at the same average coke level, as shown by Curve 2 (the middle curve) of FIG. 2.

Based on the preceding discussion, it is clear that the regeneration rate of catalyst will have a significant impact on the overall activity of the average catalyst in the reactor. Because the average residence time of the catalyst is on the order of 10-30 minutes, the effect on reactor coke level following a change in the regeneration rate will be relatively slow, on the order of the residence time. Because of this relationship, the measurement of the average coke level of catalyst is not a good indication of the activity of the catalyst in the reactor during a transient in the regeneration rate. In other words, a change in the regeneration rate of the catalyst will result in a quicker response in the activity of the catalyst in the reactor than will be the effect on the measured coke level of catalyst in the reactor.

The choice of the manipulated variable that adjusts catalyst activity will depend upon the regeneration mode. In the full regeneration mode, the catalyst flow rate to/from the regenerator is manipulated to control activity in the reactor. In the partial regeneration mode, the air rate to the regenerator is manipulated to control activity in the reactor.

Figure 3:
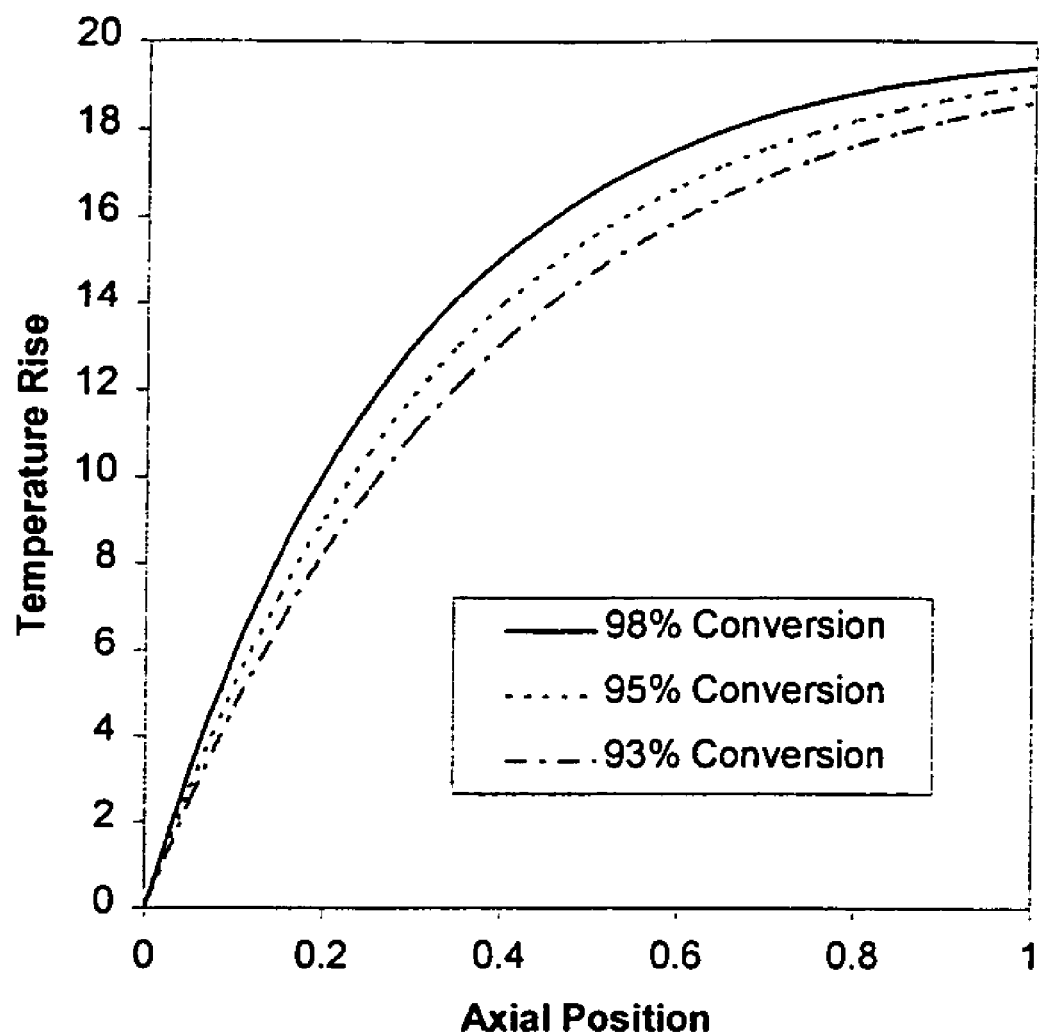
FIG. 3 depicts temperature rise in an oxygenates to olefins reactor versus axial position in an adiabatic plug flow reactor with uniform catalyst composition.

FIG. 3 depicts the relationship of temperature profile versus conversion in an adiabatic, plug flow reactor at constant space velocity at various values of the activity rate constant. These curves are expressed by the following equation:

$$T-T_0 = \Delta T(1-e^{-k\tau})$$

where T is the temperature at any axial position, $T_0$ is the feed temperature (after mixing with the catalyst), k is the 1$^{st}$ order rate constant (activity), and $\tau$ is the space time (defined previously), which is assumed here to vary linearly with the conversion. $\Delta T$ is the temperature rise for 100% conversion of the feed reactant. The value of $\Delta T$ depends upon the circulation rate of catalyst and the heat of reaction. The circulation rate of catalyst can be selected to achieve a desired value of $\Delta T$, which is selected here to be 20° C. The scale for axial position is selected such that 0 is the reactor inlet and 1 is the reactor outlet.

FIG. 3 shows that for a fixed feed temperature and catalyst circulation rate, the outlet temperature will vary with conversion. Therefore, the reactor effluent temperature could be used as an indirect measurement of the conversion in the reactor. However, an improvement in the sensitivity of the indirect conversion measurement can be achieved by selecting a different axial position for the temperature measurement. Assuming the desired conversion level is 95%, then FIG. 4 shows the difference between the actual temperature and the desired temperature at 98% and 93% conversion.

Figure 4:
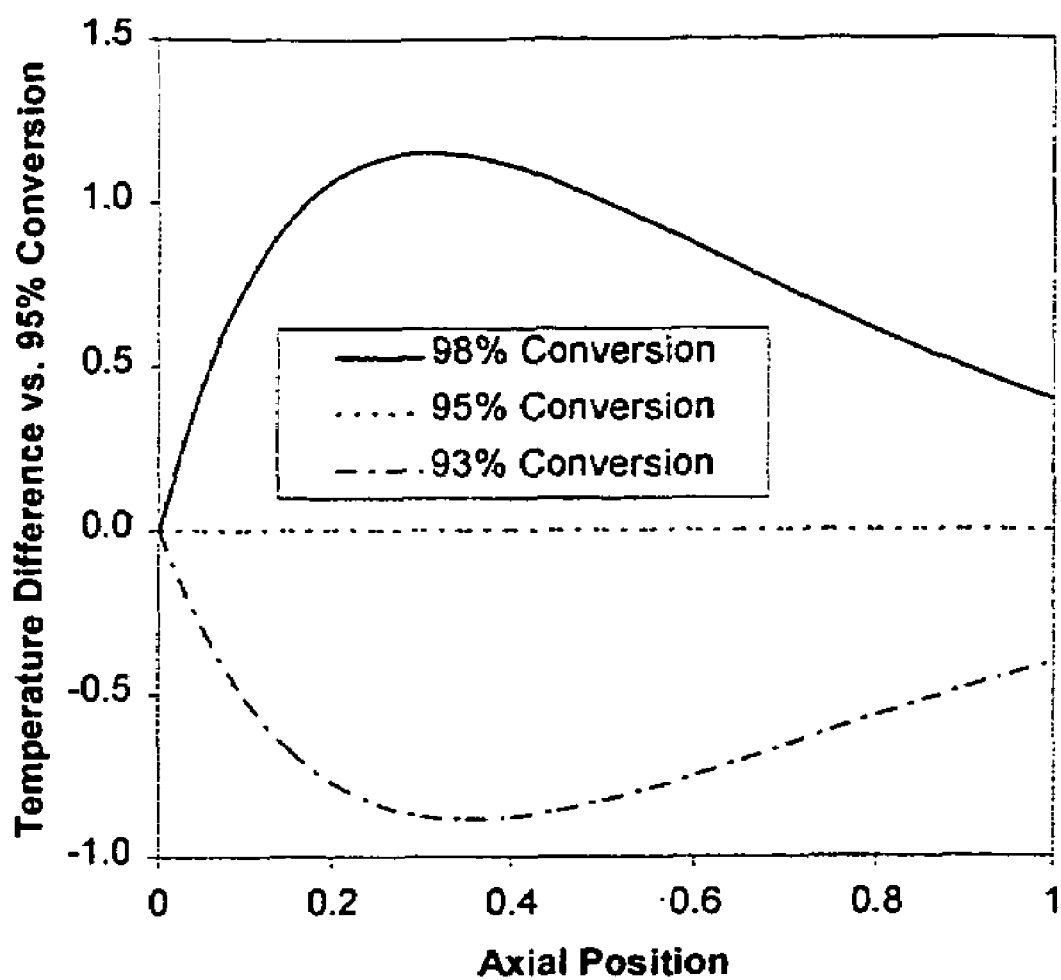
FIG. 4 depicts temperature difference for an actual temperature profile and profile at 95% conversion versus axial position, versus axial position in the reactor.

As can be seen in FIG. 4, a selection of a control temperature point at a mid-level location will give a greater sensitivity to the conversion than that of an effluent temperature. The maximum sensitivity occurs at an axial position 30-40% of the distance from the feed entrance.

An alternate method to infer reactor conversion can be achieved by measurement of a temperature profile over the axial length of the riser reactor. The conversion in the reactor is a function of the rate of temperature rise along a length of the riser, particularly near the inlet. Two or more temperature instruments within the riser may be used to calculate a rate of temperature rise versus height of the riser. This temperature rise slope is a function of the conversion; with higher slopes corresponding to higher conversion. The rate of temperature rise is also a function of the catalyst circulation rate. This effect can be eliminated by "normalizing" the slope by the total temperature rise in the reactor. That is, the slope of the temperature rise at a given axial position is divided by the total temperature rise in the riser. This variable may then be calibrated against reactor conversion and used as a set variable in the control scheme.

It should be noted that the use of the temperature to infer the conversion is most useful for plug flow reactors, such as a circulating fluid bed, high space velocity reactor. In a low space velocity, dense fluid bed reactor, the high thermal mass of the catalyst in the reactor, coupled with a backmixed flow regime, makes the use of temperature to infer conversion less practical.

EXAMPLE 1

A preferred embodiment of a riser reactor configuration for use in the present invention is depicted generally in FIG. 1. A methanol feed passed via line 12 is at least partially vaporized in a preheater 14 wherein heat is provided through a heating medium via line 16, controlled by control valve 18. The preheated feed is passed via line 20 and its flow measured by flow controller FC, which measurement is used to derive a signal controlling feed flow control valve 24 for the purpose of controlling methanol feed flow to the riser reactor 26 via feed inlet 28. Control valve 18 is manipulated for the purpose of controlling heat input to the feed by the heating medium in order to control feed preheat rate. One means of measuring the heat content of the feed is by measuring the temperature at temperature controller TC at line 20.

The methanol feed is mixed in the bottom of riser reactor 26 with regenerated catalyst introduced via line 32 to the disengaging vessel 34 and thence via line 36 along with coked catalyst collected by the disengaging vessel 34. The disengaging vessel separates solid catalyst particles that are circulated via line 36 to the bottom of riser reactor 26.

Pressure drop is determined by pressure controller (dPC) 38 which is provided with readings taken from upper riser reactor pressure sensor 40 and lower riser reactor pressure sensor 42. Pressure controller 38 integrates the readings and provides a signal for controlling valve 44 which controls the catalyst flow to the bottom of the riser reactor 26 and thus the amount of catalyst in the reaction zone.

A temperature controller 30 and temperature sensor TC 46, which sensor is positioned at a point in the intermediate portion of the riser reactor between the upper and lower ends of the riser reactor to provide a signal relating to catalyst holdup, which the controller controlling catalyst circulation slide control valve 48 to regulate the flow of regenerated catalyst 50 from regenerator 52. Regenerator flue gas is taken off via line 54, regenerator air is supplied to the reactor via line 56 and coked catalyst is directed from disengaging vessel 34 to regenerator 52 via line 58. Reactor effluent exits disengaging vessel 34 via a reactor effluent line.

EXAMPLE 2

The present invention was used to estimate the reactor conversion based on functions based on one or more temperatures in a riser of a methanol to olefins reactor. The reactor has a six inch diameter and operates at about 25 hr$^{-1}$ WHSV. A first embodiment of the present invention provided a method to control conversion utilizing a single temperature at a mid-point in the riser. In one embodiment, the single measurement can be taken from a mid-point located at from about 20% to about 80% of the reactor's axial length, say from about 40% to 60%, e.g., about 50%, wherein the reactor inlet is taken to be located at 0% and the reactor outlet at 100%. This method worked well when operating at a single condition, wherein feed enthalpy and catalyst circulation rates remained constant. However, the single mid-point measurement alone was less effective in controlling conversion transitioning between operating conditions of significantly differing feed enthalpy and catalyst circulation rates inasmuch as varying these conditions affects reactor mid-temperature, not just conversion.

Accordingly, a second embodiment of the present invention was made, wherein a series of axial temperature measurements in the riser of a methanol to olefins reactor were taken and a temperature profile developed. The second embodiment has been shown to reliably estimate conversion independent of how the feed enthalpy or catalyst circulation rates change.

Figure 5:
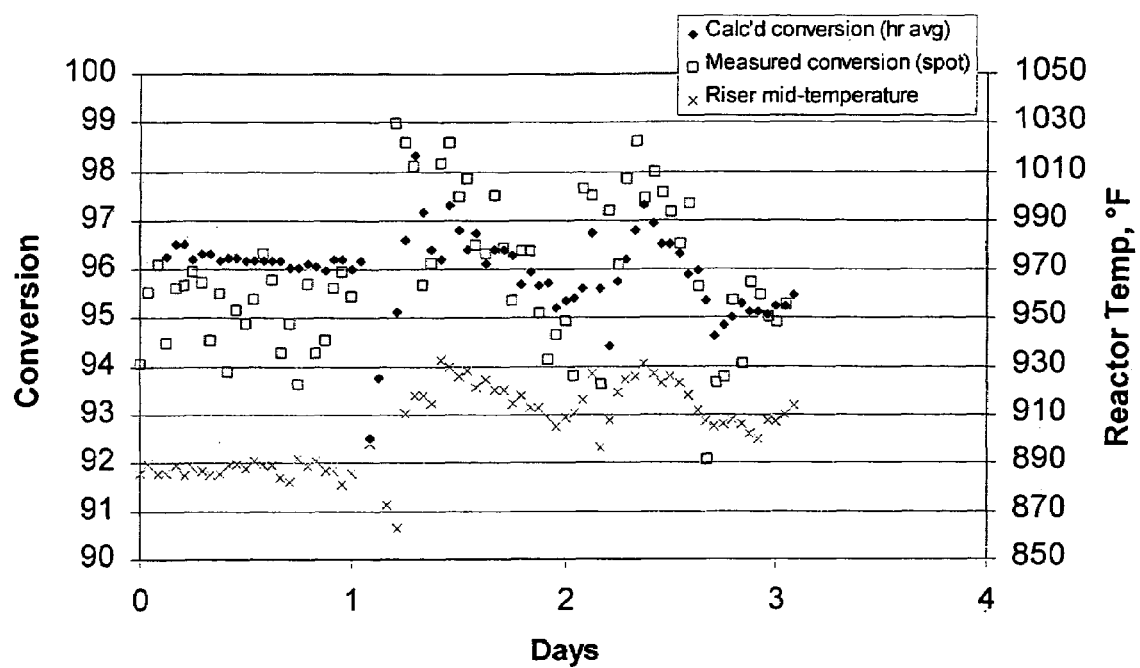
FIG. 5 depicts a comparison of calculated conversion (hourly average), measured conversion (spot) and riser midtemperature (° F.) for a pilot plant during a four day period during which a transition in reactor conditions was made. The data indicate that the present invention provides a calculated conversion (based on a series of actual temperature measurements in the riser) correlates well with the measured conversion.over a period of four days.

FIG. 5 shows the calculated and measured conversions during a transition in reactor conditions over a four day period. The calculated conversion trended well with the measured conversion, showing that the method of the present invention using a series of axial temperature measurements in the riser should be useful for real-time control of conversion. Of course, the analyzer results will be used to adjust the set point in the conversion controller based on actual measured results.

Conversion was calculated from a reactor temperature profile as follows:

Conversion, X, in a first order reaction with plug flow is a function of the rate constant, k, and the space-time, τ.

$$X = 1 - e^{-k\tau} \quad (1)$$

If the heat of reaction does not vary significantly as the reaction proceeds, the temperature in a plug flow reactor can be assumed to be proportional to the conversion as follows, $$T = T_i + X \cdot \Delta T_{100} \quad (2)$$

where T is the temperature at any point, $T_i$ is the inlet temperature, and $\Delta T_{100}$ is the temperature rise that would be obtained at 100% conversion. $\Delta T_{100}$ can be approximated as follows, where $X_O$ is the conversion at the reactor outlet.

$$\Delta T_{100} = \frac{\Delta T_{act}}{X_o} \quad (3)$$

A dimensionless temperature, θ, and a dimensionless axial position z are defined. Here, h is the actual axial dimension and H is the total axial height.

$$\theta = \frac{T - T_i}{\Delta T_{100}}, \quad z = \frac{h}{H} \quad (4)$$

The dimensionless temperature profile is equated with the dimensionless conversion profile, thus:

$$\theta(z) = 1 - \exp(-k\tau z) \quad (5)$$

where θ(z) is the dimensionless temperature at position z. This dimensionless curve is unique for a given conversion, and does not depend on any other parameters. Therefore, we can estimate the conversion from an analysis of the temperature profile in the reactor. θ can be differentiated with respect to z to obtain the slope of the dimensionless temperature profile curve at any position z.

$$\frac{d\theta}{dz} = k\tau \cdot \exp(-k\tau z) \quad (6)$$

The product kt is unique for a desired conversion level, $X_O$. Equation (1) can be rearranged as follows.

$$k\tau = -\ln(1-X_o) \quad (7)$$

Substituting (7) into (6) gives $$\frac{d\theta}{dz} = -\ln(1-X_o) \cdot (1-X_o)^z \quad (8)$$

This equation cannot be solved explicitly for $X_O$. However, we can solve this equation for one of the $X_O$ terms as follows.

$$X = 1 - \exp\left(-\frac{\frac{d\theta}{dz}}{(1-X_o)^z}\right) \quad (9)$$

Equation (9) can thus be used as an estimation of the conversion in the reactor. The $d\theta/dz$ term is the dimensionless slope of the temperature profile curve at a point z in the riser. One method for estimating this value from riser temperature data is set out below in TABLE 2. The desired conversion (or set point) is used for the $X_O$ value on the right hand side of the equation. The dimensionless temperature profile requires a measure of the reactor inlet temperature, which is the adiabatic temperature of the feed vapor and recycle catalyst mixture before any reaction proceeds. This temperature is difficult to measure. As shown in TABLE 2 below, this temperature is estimated from a backwards extrapolation of the riser temperature data.

TABLE 2

Conversion Calculation Method for MTO Pilot Plant

Measured Variables

| | |
|---|---|
| T1 | Riser temperature at z = 0.057 |
| T2 | Riser temperature at z = 0.115 |
| T3 | Riser temperature at z = 0.173 |
| T4 | Riser temperature at z = 1.0 |

Input Variables

| | |
|---|---|
| SP | Desired conversion set point (percent) |
| Z2 | Dimensionless location of point where slope is measured (at T2) = 0.115 |
| DZ | Dimensionless distance between points T1, T2, and T3 (assuming equal-distant) = 0.058 |

Calculations

| | |
|---|---|
| Inlet temperature[1] | Ti = 2 * T1 − T2 |
| Outlet temperature | To = T4 |
| Slope at z = 0.115 | DTDZ = (T3 − T1)/(To − Ti)/(2 * DZ) * SP/100 |
| Calculated conversion | XPV = [1 − exp(−1 * DTDZ/(1 − SP/100) ^ Z2)] * 100 |

[1]The inlet temperature is estimated by linear extrapolation of the temperatures at z = 0.058 and z = 0.115 back to z = 0

FIG. 5 shows pilot plant data over a time period that begins with lined-out operation at 95% conversion, goes through a significant transition in reactor conditions, and ends in another lined-out condition at ~95% conversion but at a different reactor temperature and catalyst circulation rate. These data are in an "open-loop" mode, in which the calculated conversion does not automatically manipulate any variables. The open squares are measured conversion data from hourly gas chromatograph (GC) samples. The GC requires nearly an hour to complete each analysis, preventing these measurements from being useful for real-time control. The diamonds show the calculated conversion based on equation (9), and the X's show the riser mid-point temperatures. Although the X's trend with actual conversion, the beginning and ending temperatures are about 10° F. different from each other, while the actual conversions are the same. On the other hand, the calculated conversion at the beginning and end conditions are within about 1% of the actual conversion.

These data show that the dimensionless temperature profile can serve as a useful inference of conversion to use for closed-loop control. Although the riser mid-temperature can be used for control of conversion at a single operating condition, it is not useful for controlling conversion when reactor conditions (e.g., temperature or catalyst circulation rates) are being changed.

Once the conversion and the temperature rise of the reactor are calculated, it is straightforward to estimate the cat:oil ratio based on the knowledge of the heat of reaction and the heat capacity of the catalyst. This calculation, presented TABLE 3 below, assumes that the heat capacity of the vapors in the reactor is small relative to the heat capacity of the catalyst. This is a reasonable assumption based on the fact that the mass ratio of catalyst to vapor is on the order of 20:1.

TABLE 3

Cat:Oil Calculation Method for MTO Pilot Plant

Input Variable

| | |
|---|---|
| DHCP | Heat of reaction relative to heat capacity of catalyst = $\Delta H_{rxn}/C_{Pcat}$ ~1727° F. |

Calculation

| | |
|---|---|
| Cat:Oil ratio | CATOIL = DHCP * XPV/(To − Ti) |

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. An oxygenates to olefins fluidized bed reactor apparatus for converting an oxygenate feed to olefins in a riser reactor which comprises:

(a) an oxygenate feed line communicating with a riser reactor feed inlet to said riser reactor, said riser reactor further comprising a riser reactor outlet for riser reactor effluent containing solid catalyst particles and olefins-containing vapor;

(b) a preheater through which said oxygenate feed line passes for at least partially vaporizing said feed by heat exchange with a fluid heating medium flowing through said preheater;

(c) a disengaging vessel for receiving said riser reactor effluent and separating at least some of said solid catalyst particles from said effluent, said disengaging vessel further comprising a disengaging vessel outlet at an upper portion of said vessel for removing said olefins-containing vapor;

(d) a catalyst circulation line running downward from a lower portion of said disengaging vessel to a lower portion of said riser reactor;

(e) a regenerator comprising a lower inlet for introducing a regeneration medium, an upper outlet for regenerator flue gas, said regenerator further comprising a first catalyst transport line running downwardly from a lower portion of said disengaging vessel to a regenerator catalyst inlet on the regenerator, and a second catalyst transport line extending downwardly from a regenerated catalyst outlet on the regenerator and intersecting with a lift gas riser, said lift gas riser having an upper outlet at said disengaging vessel anti a lower lift gas inlet; and (f) a regenerator catalyst circulation control valve means for controlling the passage of catalyst from said regenerated catalyst outlet to said lift gas riser, and being manipulated as a function of riser set reactor temperature; and (g) a catalyst circulation control valve means for controlling circulation of catalyst from said disengaging vessel to said riser reactor, and being manipulated as a function of the difference in pressure between an upper portion of said riser reactor and a lower portion of said riser reactor.

2. The apparatus of claim 1, wherein said riser reactor comprises a temperature sensor at a point ranging from 30% to 40% of said riser reactor length, measured from said feed inlet of the riser reactor.

3. The apparatus of claim 1, wherein said riser reactor comprises a temperature sensor at a single location between about 20% to about 80% of the axial length of the reactor.

4. The apparatus of claim 1, wherein said riser reactor comprises a temperature sensor along a portion of the reactor.

5. The apparatus of claim 1, wherein said catalyst circulation control valve means for controlling circulation of catalyst includes a pressure controller that integrates readings taken from an upper riser reactor pressure sensor and a lower riser reactor pressure sensor and controls catalyst amount in the riser reactor.

* * * * *